United States Patent
Grazioso et al.

(10) Patent No.: US 7,737,407 B2
(45) Date of Patent: Jun. 15, 2010

(54) METHOD AND APPARATUS FOR PROVIDING DEPTH-OF-INTERACTION DETECTION USING POSITRON EMISSION TOMOGRAPHY (PET)

(75) Inventors: Ronald Grazioso, Knoxville, TN (US); Mehmet Aykac, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/772,909

(22) Filed: Jul. 3, 2007

(65) Prior Publication Data

US 2009/0008562 A1  Jan. 8, 2009

(51) Int. Cl.
*G01T 1/166* (2006.01)
*G01T 1/20* (2006.01)

(52) U.S. Cl. .................. 250/363.04; 250/366
(58) Field of Classification Search ............ 250/363.04, 250/370.11, 366, 367, 363.02, 362
See application file for complete search history.

(56) References Cited

U.S. PATENT DOCUMENTS

| 6,124,595 | A  | * | 9/2000 | Engdahl et al. | 250/366 |
| 6,180,946 | B1 | * | 1/2001 | Ebstein | 250/370.11 |
| 6,906,329 | B2 | * | 6/2005 | Bryman | 250/366 |
| 2005/0016950 | A1 | * | 1/2005 | Andreaco et al. | 216/24 |
| 2009/0032717 | A1 | * | 2/2009 | Aykac et al. | 250/367 |
| 2009/0039268 | A1 | * | 2/2009 | Peter et al. | 250/363.04 |
| 2009/0134334 | A1 | * | 5/2009 | Nelson | 250/361 R |

* cited by examiner

*Primary Examiner*—David P Porta
*Assistant Examiner*—Faye Boosallis
(74) *Attorney, Agent, or Firm*—Peter L. Kendall

(57) ABSTRACT

A detector is provided for nuclear medicine imaging. Scintillator pixels form an axial array and a transaxial array. A first photosensor is positioned along the axial array; and a second photosensor is positioned along the transaxial array, wherein the first photosensor and the second photosensor provide dual event localization for nuclear medicine imaging.

19 Claims, 6 Drawing Sheets

METHOD AND APPARATUS FOR PROVIDING DEPTH-OF-INTERACTION DETECTION USING POSITRON EMISSION TOMOGRAPHY (PET)

FIELD OF THE INVENTION

The present invention, according to certain embodiments, relates to nuclear medicine imaging.

BACKGROUND OF THE INVENTION

Medical radionuclide imaging, commonly referred to as nuclear medicine, is a significant diagnostic tool that involves the use of ionizing radiation to obtain accurate imaging of an in vivo patient. Typically, one or more biologically appropriate radiopharmaceuticals are administered to a patient, as by ingestion, inhalation, or injection. Tracer amounts of these radioactive substances emanate gamma quanta while localizing at specific organs, bones, or tissues of interest within the patient's body. One or more radiation detectors (e.g., positron emission tomography (PET) detector) are then used to record the internal spatial distribution of the radiopharmaceutical as it propagates from the study area. Known applications of nuclear medicine include: analysis of kidney function, imaging blood-flow and heart function, scanning lungs for respiratory performance, identification of gallbladder blockage, bone evaluation, determining the presence and/or spread of cancer, identification of bowel bleeding, evaluating brain activity, locating the presence of infection, and measuring thyroid function and activity. Hence, accurate detection is vital in such medical applications.

In position emission tomography (PET), certain detectors utilize a scintillator array and an array of photosensors to provide event localization within the scintillator array for 2-dimensional (2-D) imaging. However, it is readily apparent that 3-D information can be very advantageous, particularly in the above medical applications. With 3-D information, parallax errors can be reduced or eliminated within enough spatial resolution in the transaxial direction.

Traditionally, a monolithic scintillator can be used to obtain 3-D information. Unfortunately, this approach has the drawback of a reduced active area due to "edge effects." That is, near edges (or corners) photons are not easily directed and can result in misinformation, thereby negatively impact imaging; notably the resolution is reduced. That is, when gamma interactions occur near the edges of monolithic scintillators, the light produced is not channeled or collected properly which can result in poor event localization. Monolithic blocks also suffer from poor event localization when the incoming gamma ray is at oblique angles to the front surface of the detector.

Based on the foregoing, there is a clear need for an improved detector for nuclear medicine imaging.

DISCLOSURE OF THE INVENTION

According to certain embodiments, a detector is provided that employs a positron emission tomography (PET) scintillation block, which supplies depth-of-interaction (DOI) information. The DOI information is acquired by reading out two or more sides of a scintillation array, where the scintillation array has alternating transaxial and axial linear arrays of pixellated scintillators. This arrangement advantageously minimizes the edge effects and increases resolution.

Additional advantages of the present invention will become readily apparent to those skilled in the art from the following detailed description, wherein embodiments of the present invention are described, simply by way of illustration of the best mode contemplated for carrying out the present invention. As will be realized, the present invention is capable of other and different embodiments and its several details are capable of modifications in various obvious respects, all without departing from the present invention.

BRIEF DESCRIPTION OF THE DRAWINGS

Various exemplary embodiments are illustrated by way of example, and not by way of limitation, in the figures of the accompanying drawings in which like reference numerals refer to similar elements and in which.

DESCRIPTION OF THE PREFERRED EMBODIMENTS

A method and apparatus for providing depth-of-interaction detection using position emission tomography (PET) are described. In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Figure 1:
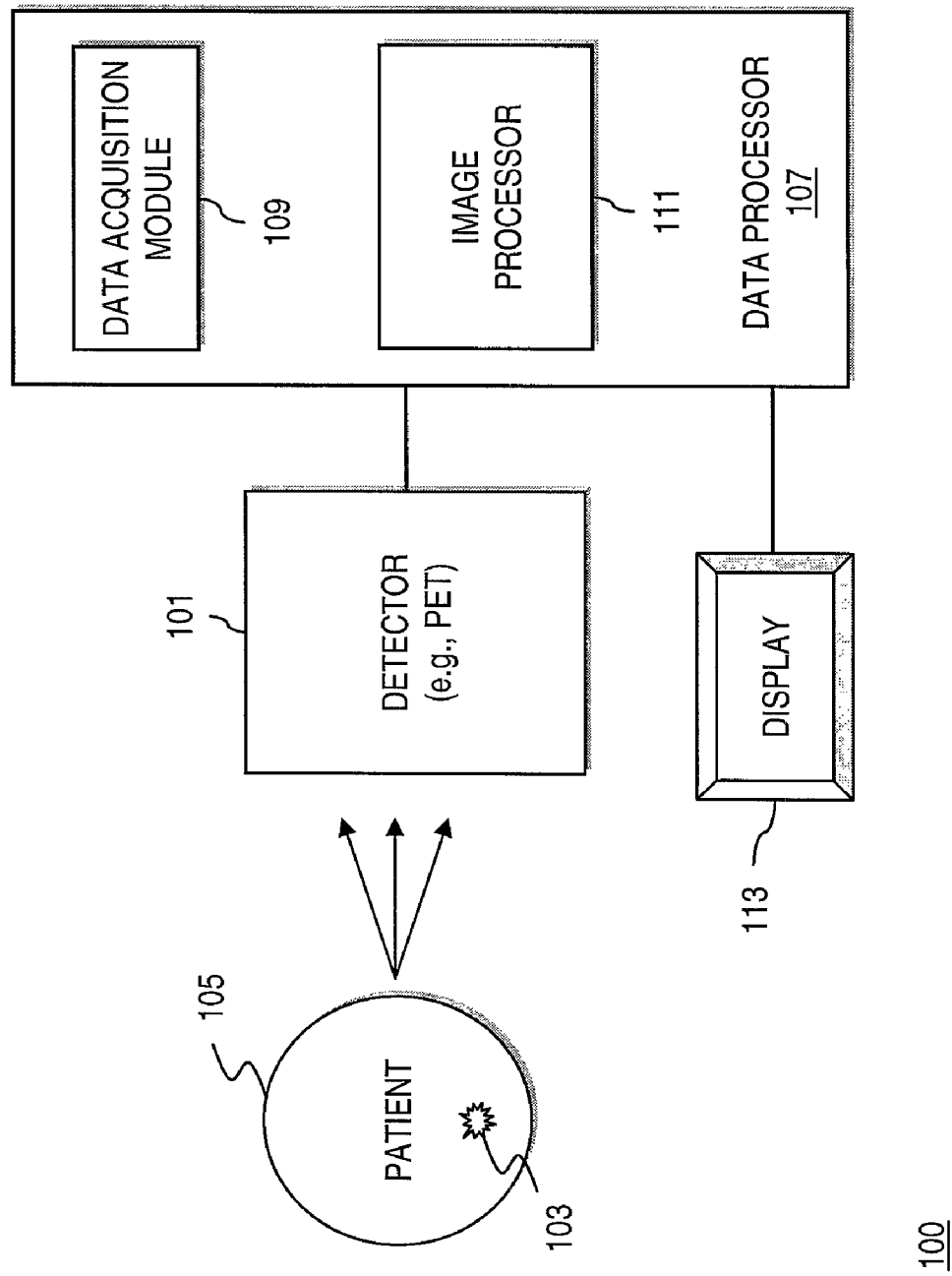
FIG. 1 is a diagram of a detection system utilizing a positron emission tomography (PET) scintillation block for generating depth-of-interaction information, according to various embodiments.

FIG. 1 is a diagram of a detection system utilizing a PET scintillation block for generating depth-of-interaction information, according to various embodiments. As shown, a detection system 100 includes a detector 101 to observe events stemming from a radiation source 103 emitting radiation (e.g., gamma rays) from a subject (patient) 105. The detector 101 outputs data to a data processor 107, which includes a data acquisition module 109 and an image processor 111. The data acquisition module 109 uses spatial coordinate signals to produce input to the image processor 111. The image processor 111 can then produce, for example, an image of tissues in the patient 105. The image can then be displayed on a display unit 113.

The system 100, according to certain embodiments, utilizes a positron emission tomography (PET) scintillation block, which provides 3 dimensional (3D) imaging—i.e. depth-of-interaction (DOI) information. The linear arrays of the block share light between each other. In an exemplary embodiment, the axial arrays is readout by one set of photosensors, while the transaxial arrays would be readout by another independent set of photosensors. This capability to localize data is as more fully described in FIGS. 2-5.

Figure 2:
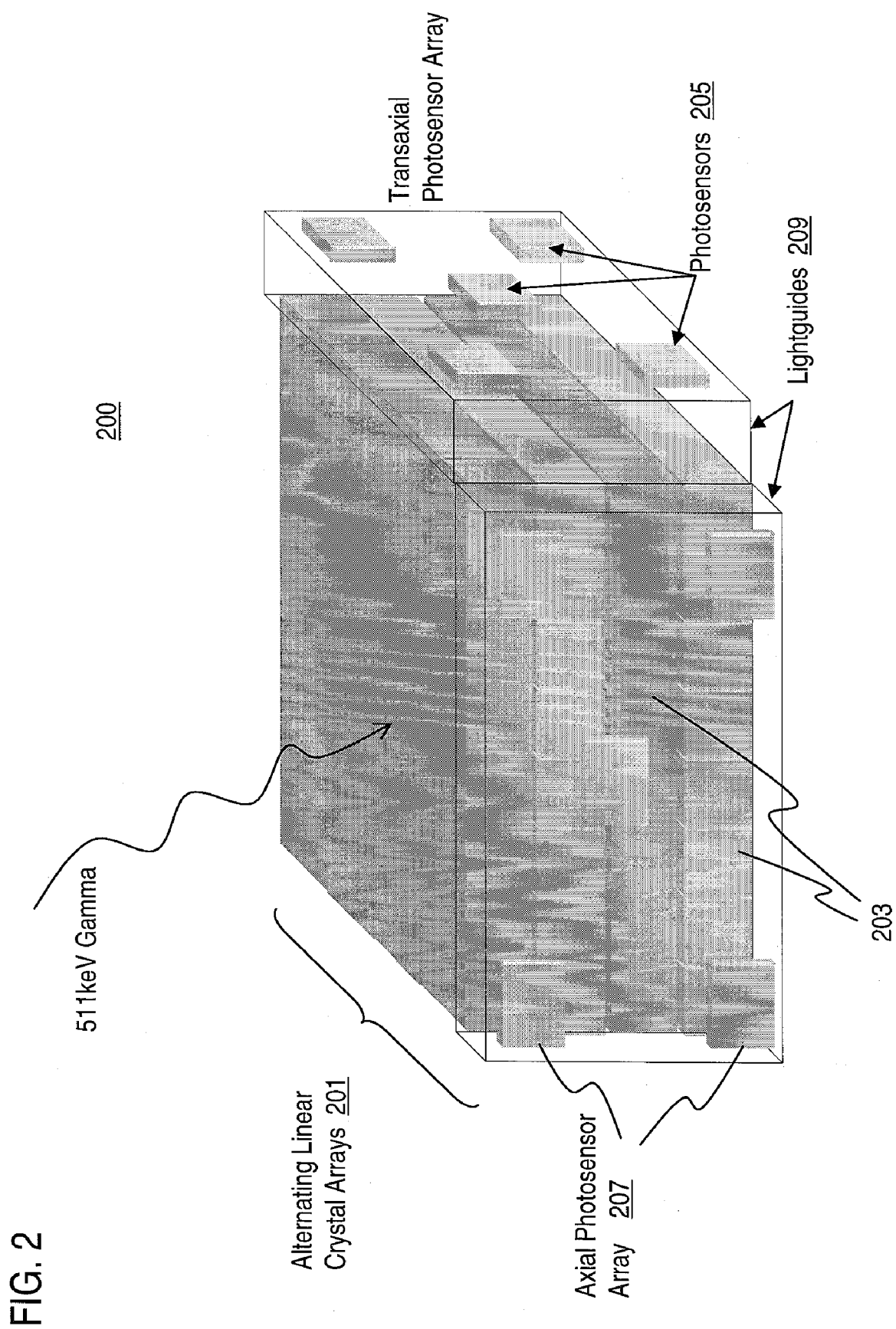
FIG. 2 is a PET scintillation block used in the system of FIG. 1, according to an exemplary embodiment.

FIG. 2 is a PET scintillation block used in the system of FIG. 1, according to an exemplary embodiment. The associated process is explained in FIG. 3. Continuing with the example of FIG. 1, the DOI information is acquired, by the data acquisition module 109, by reading out two or more sides of a scintillation array 201, where the scintillation array 201 has alternating transaxial and axial linear arrays of pixellated scintillators 203. The light from a gamma interaction within a single scintillator pixel 203 produces light in at least one pixel of each of the transaxial and axial arrays, thereby producing a X and Y readout that can be used to find the X, Y and Z position of the event within the scintillation array. At this point, localization data is acquired by the data acquisition module 109 and processed by the image processor 111, per steps 301 and 303.

The detector 101 utilizes alternation transaxial and axial linear arrays, optically coupled to provide DOI information. According to one embodiment, photosensors 205 are placed on two or more sides of the scintillator array to provide dual event localization so the gamma interaction can be localized in all three dimensions. When a gamma interaction occurs within one of the scintillator pixels 203 within the block 200, light is produced within that particular crystal. The light will spread in all directions, with the majority of the light traveling towards the small end of the crystal and into one array of photosensors 205. However, because the light is shared between the pixels 203, some of the light will be coupled into the pixels touching the initial pixel. The pixels, which are optically coupled to the interaction pixel, are the axial pixels (assuming, in this case, the pixel of interaction is a transaxial pixel). The light coupled into the optically coupled axial pixels will travel down the pixels to the second set of photosensors 207. Both photosensor sets 205, 207, as positioned via lightguides 209, are used to determine their respective 2-D event locations (i.e., Z,Y for the transaxial location and X,Y for the axial location). In other words, both events can be used together to determine the gamma energy and location within the scintillator array (X,Y,Z) that the gamma event was absorbed. The pixellated scintillators 203 confine light better than the traditional monolithic scintillator block design, and can more readily distribute light among the photosensors 205, 207.

As shown, the sets of photosensors 205, 207 include an arrangement of sensors in each corner and the center. However, it is contemplated that a variety of arrangements can be used, such as an even distribution of sensors in an n×n pattern (n being an integer; with n rows and n columns). From a cost perspective, minimizing the number of photosensors is desirable.

Conceptually, this approach can be viewed as a simplified version of a monolithic scintillator block.

After receiving the acquired localization data, the image processor 111 can convert the localization data into 3-D images, as in step 305.

Figure 3:
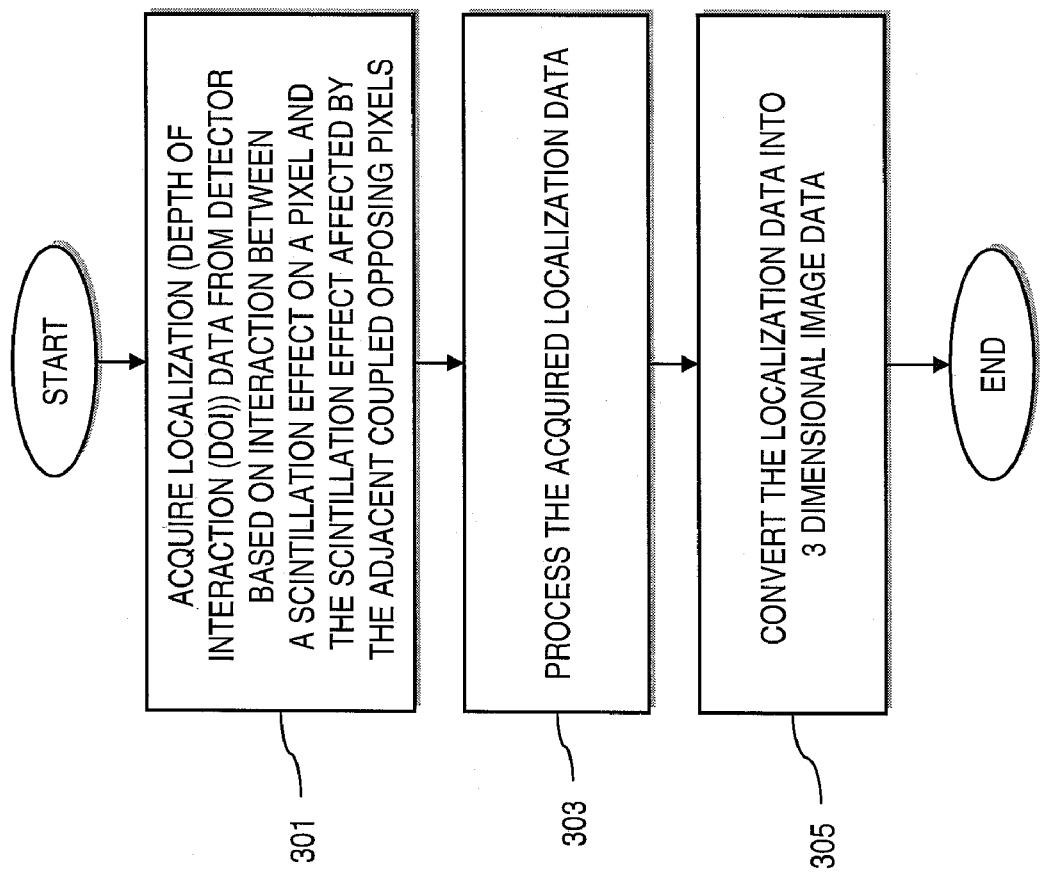
FIG. 3 is a flowchart of a detection process performed by the system of FIG. 1, according to an exemplary embodiment.
Figure 4:
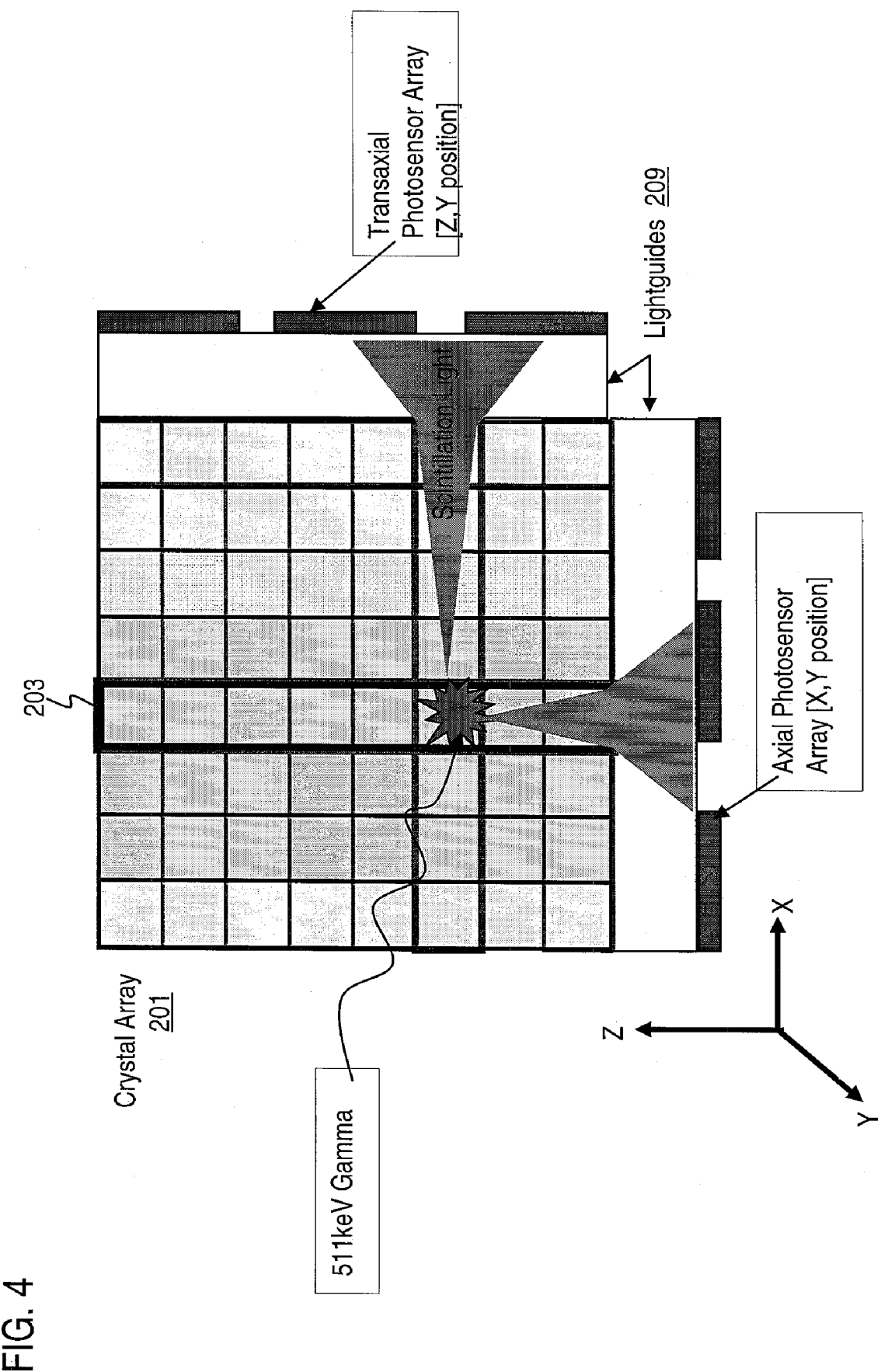
FIG. 4 is a diagram of a top view of the scintillation array of FIG. 3, according to an exemplary embodiment.

FIG. 4 is a diagram of a top view of the scintillation array of FIG. 3, according to an exemplary embodiment. Under this scenario, a photon, gamma ray (having e.g., 511 keV), interacts with one crystals 203 and the light produced from the scintillation effect would be coupled into the adjacent opposing crystals. The light in the first pixel provides information to locate the event in the Z,Y dimensions; conversely, the light shared to the secondary (opposing) pixels provides information to locate the event in the X,Y dimensions. Both sets of information provide the X,Y, Z location of the event. The sum of these two sets of photosensors is used for energy and timing discrimination.

Figure 5:
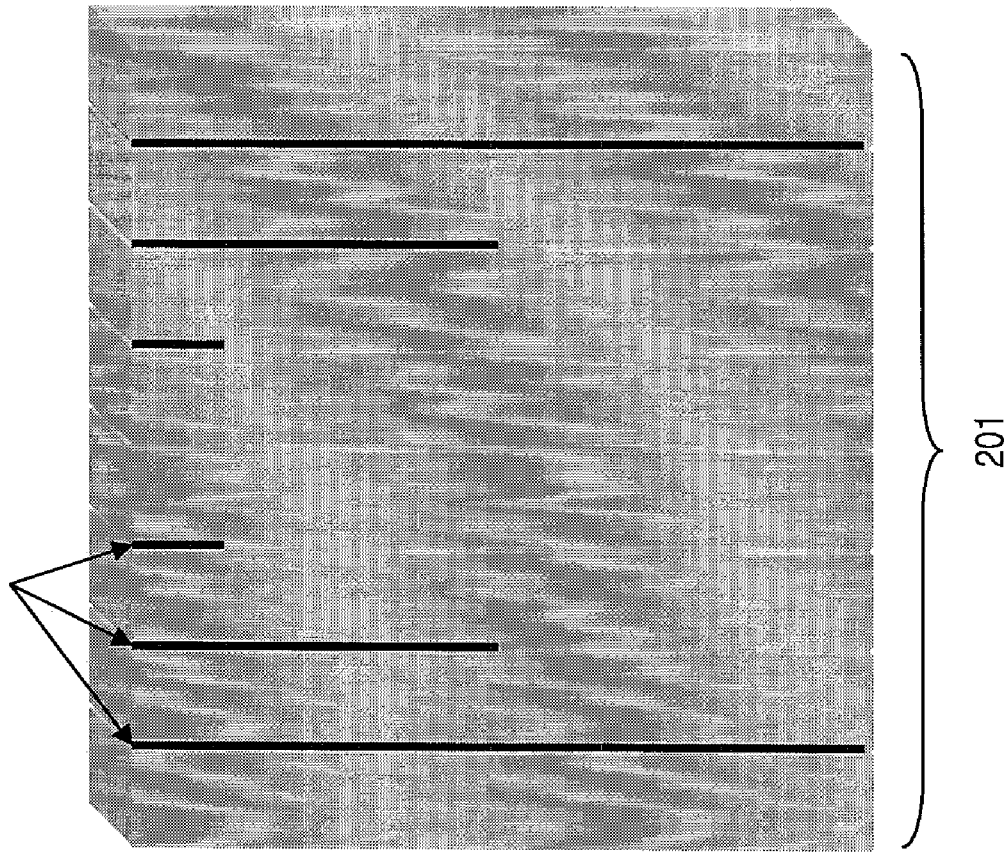
FIG. 5 is a diagram of a linear crystal array with varying reflective partitions, according to an exemplary embodiment.

FIG. 5 is a diagram of a linear crystal array with varying reflective partitions, according to an exemplary embodiment. For the proper light sharing between the linear arrays 201 to occur, little to no reflective partitions between the linear arrays 201 are used, according to certain embodiments, so that light sharing in both axial and transaxial directions can occur. However, according to various exemplary embodiments, reflective partitions 501 within the pixels in the linear arrays 201 can be utilized to optimize crystal identification. This improves readouts of the linear arrays 201, thus increasing dynamic range. The application of the reflective partitions and determination of the particular lengths are dictated, in part, by the type of scintillators and their geometric arrangement.

The data and imaging processes described herein may be implemented via software, hardware (e.g., general processor, Digital Signal Processing (DSP) chip, an Application Specific Integrated Circuit (ASIC), Field Programmable Gate Arrays (FPGAs), etc.), firmware or a combination thereof. Such exemplary hardware for performing the described functions is detailed below.

Figure 6:
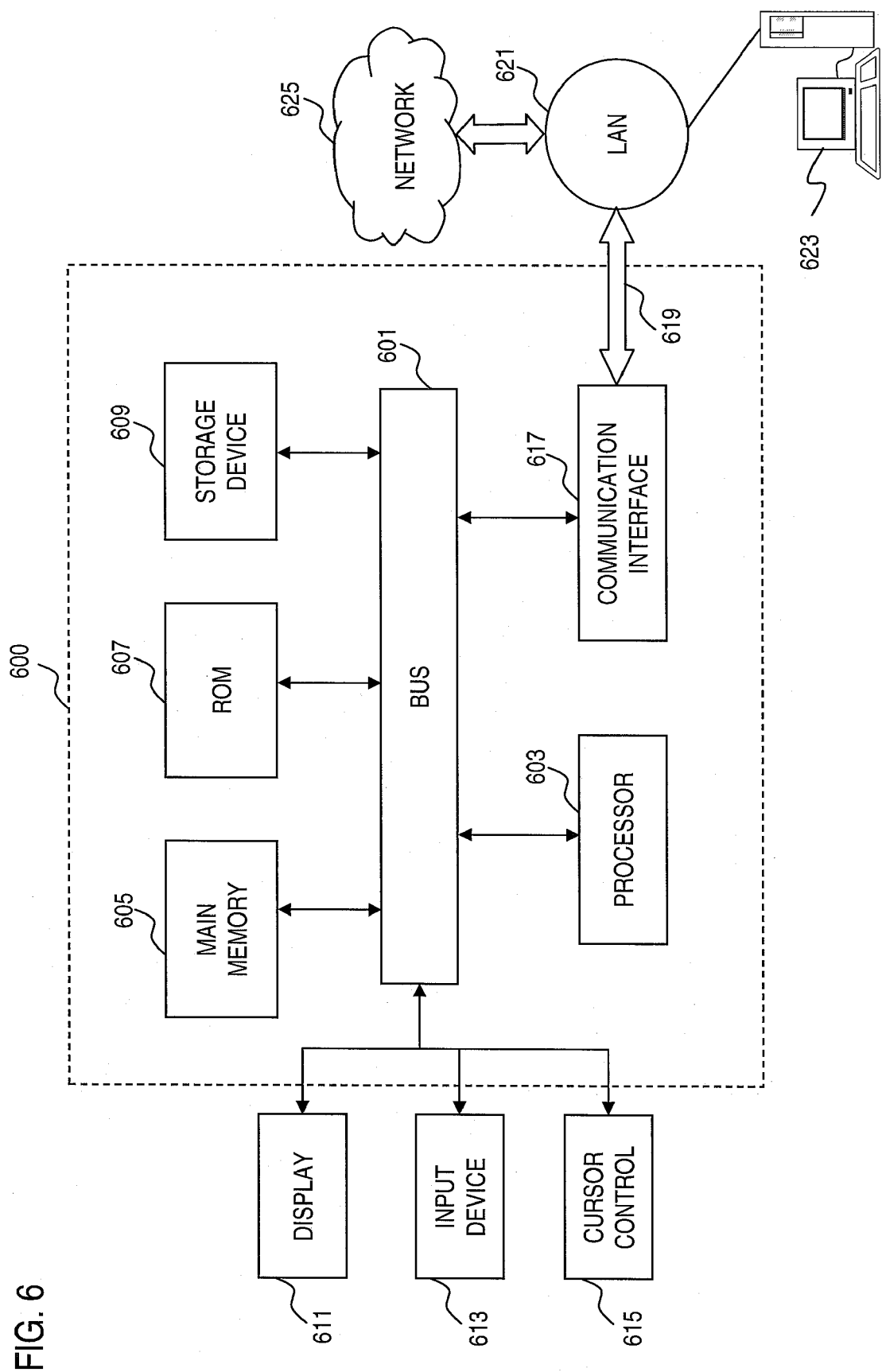
FIG. 6 is a diagram of a computing hardware that can be used to implement various embodiments of the invention.

FIG. 6 illustrates a computing hardware 600 upon which an embodiment according to various exemplary embodiments can be implemented. For example, the processes described herein can be implemented using the computer system 600. The computer system 600 includes a bus 601 or other communication mechanism for communicating information and a processor 603 coupled to the bus 601 for processing information. The computer system 600 also includes main memory 605, such as a random access memory (RAM) or other dynamic storage device, coupled to the bus 601 for storing information and instructions to be executed by the processor 603. Main memory 605 can also be used for storing temporary variables or other intermediate information during execution of instructions by the processor 603. The computer system 600 may further include a read only memory (ROM) 607 or other static storage device coupled to the bus 601 for storing static information and instructions for the processor 603. A storage device 609, such as a magnetic disk or optical disk, is coupled to the bus 601 for persistently storing information and instructions.

The computer system 600 may be coupled via the bus 601 to a display 611, such as a cathode ray tube (CRT), liquid crystal display, active matrix display, or plasma display, for displaying information to a computer user. An input device 613, such as a keyboard including alphanumeric and other keys, is coupled to the bus 601 for communicating information and command selections to the processor 603. Another type of user input device is a cursor control 615, such as a mouse, a trackball, or cursor direction keys, for communicating direction information and command selections to the processor 603 and for controlling cursor movement on the display 611.

According to one embodiment contemplated herein, the processes described are performed by the computer system 600, in response to the processor 603 executing an arrangement of instructions contained in main memory 605. Such instructions can be read into main memory 605 from another computer-readable medium, such as the storage device 609. Execution of the arrangement of instructions contained in main memory 605 causes the processor 603 to perform the process steps described herein. One or more processors in a multi-processing arrangement may also be employed to execute the instructions contained in main memory 605. In alternative embodiments, hard-wired circuitry may be used in place of or in combination with software instructions to implement the certain embodiments. Thus, the exemplary embodiments are not limited to any specific combination of hardware circuitry and software.

The computer system 600 also includes a communication interface 617 coupled to bus 601. The communication interface 617 provides a two-way data communication coupling to a network link 619 connected to a local network 621. For example, the communication interface 617 may be a digital subscriber line (DSL) card or modem, an integrated services digital network (ISDN) card, a cable modem, a telephone modem, or any other communication interface to provide a data communication connection to a corresponding type of communication line. As another example, communication interface 617 may be a local area network (LAN) card (e.g. for Ethernet™ or an Asynchronous Transfer Model (ATM) network) to provide a data communication connection to a compatible LAN. Wireless links can also be implemented. In any such implementation, communication interface 617 sends and receives electrical, electromagnetic, or optical signals that carry digital data streams representing various types of information. Further, the communication interface 617 can include peripheral interface devices, such as a Universal Serial Bus (USB) interface, a PCMCIA (Personal Computer Memory Card International Association) interface, etc. Although a single communication interface 617 is depicted in FIG. 6, multiple communication interfaces can also be employed.

The network link 619 typically provides data communication through one or more networks to other data devices. For example, the network link 619 may provide a connection through local network 621 to a host computer 623, which has connectivity to a network 625 (e.g. a wide area network (WAN) or the global packet data communication network now commonly referred to as the "Internet") or to data equipment operated by a service provider. The local network 621 and the network 625 both use electrical, electromagnetic, or optical signals to convey information and instructions. The signals through the various networks and the signals on the network link 619 and through the communication interface 617, which communicate digital data with the computer system 600, are exemplary forms of carrier waves bearing the information and instructions.

The computer system 600 can send messages and receive data, including program code, through the network(s), the network link 619, and the communication interface 617. In the Internet example, a server (not shown) might transmit requested code belonging to an application program for implementing an exemplary embodiment through the network 625, the local network 621 and the communication interface 617. The processor 603 may execute the transmitted code while being received and/or store the code in the storage device 609, or other non-volatile storage for later execution. In this manner, the computer system 600 may obtain application code in the form of a carrier wave.

The term "computer-readable medium" as used herein refers to any medium that participates in providing instructions to the processor 603 for execution. Such a medium may take many forms, including but not limited to non-volatile media, volatile media, and transmission media. Non-volatile media include, for example, optical or magnetic disks, such as the storage device 609. Volatile media include dynamic memory, such as main memory 605. Transmission media include coaxial cables, copper wire and fiber optics, including the wires that comprise the bus 601. Transmission media can also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and EPROM, a FLASH-EPROM, any other memory chip or cartridge, a carrier wave, or any other medium from which a computer can read.

Various forms of computer-readable media may be involved in providing instructions to a processor for execution. For example, the instructions for carrying out various exemplary embodiments may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a personal digital assistant (PDA) or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on storage device either before or after execution by processor.

While the invention has been described in connection with a number of embodiments and implementations, the invention is not so limited but covers various obvious modifications and equivalent arrangements, which fall within the purview of the appended claims.

What is claimed is:

1. An apparatus comprising:
 a plurality of scintillator pixels forming an axial array and a transaxial array alternately arranged into a pixellated scintillator array;
 a first set of a plurality of photosensors positioned along the axial array; and
 a second set of a plurality of photosensors positioned along the transaxial array,
 wherein the first set of photosensors and the second set of photosensors are placed on at least two sides of the scintillator array to provide dual event localization for nuclear medicine imaging, wherein each of the first and second sets of photosensors are used to determine their respective 2-Dimensional event locations within the scintillator array.

2. An apparatus according to claim 1, wherein the axial array and the transaxial array are on adjacent sides.

3. An apparatus according to claim 1, wherein the first set of plurality of photosensors is on one of the sides, and the second set of plurality of photosensors is on another one of the sides.

4. An apparatus according to claim 3, further comprising:
 a third set of a plurality of photosensors positioned on a third one of the sides of the block.

5. An apparatus according to claim 1, further comprising:
 a plurality of reflective partitions interspersed among the scintillator pixels.

6. An apparatus according to claim 5, wherein one of the reflective partitions has a length different from another one of the reflective partitions.

7. An apparatus according to claim 1, wherein the axial and transaxial arrays are linear.

8. A system comprising:
a detector configured to generate a depth-of-interaction (DOI) information stemming from radiation emitted from a radiation source, the detector including,
a plurality of scintillator pixels forming a block of alternating arrays arranged axially and transaxially into a pixellated scintillator array,
a first set of a plurality of photosensors coupled to one side of the block in an axial direction,
a second set of a plurality of photosensors coupled to another side of the block in a transaxial direction;
wherein the first set of photosensors and the second set of photosensors provide dual event localization for nuclear medicine imaging, wherein each of the first and second sets of photosensors are used to determine their respective 2-Dimensional DOI information within the scintillator array; and
an image processor configured to generate a three dimensional image from the DOI information.

9. A system according to claim 8, wherein the one side and the other side are adjacent sides.

10. A system according to claim 9, wherein the detector further includes a third set of photosensors positioned on a third one of the sides of the block.

11. A system according to claim 8, wherein the block includes a plurality of reflective partitions interspersed among the scintillator pixels.

12. A system according to claim 11, wherein one of the reflective partitions has a length different from another one of the reflective partitions.

13. A system according to claim 8, wherein the axial and transaxial arrays are linear.

14. A method comprising:
acquiring localization data from a detector that includes,
a plurality of scintillator pixels forming an axial array and a pixellated transaxial array alternately arranged;
a first set of a plurality of photosensors positioned along the axial array; and
a second set of a plurality of photosensors positioned along the transaxial array, wherein the first set of photosensors and the second set of photosensors provide the localization data, wherein each of the first and second sets of photosensors are used to determine their respective 2-Dimensional event locations within the scintillator array; and
converting the localization data into an image.

15. A method according to claim 14, wherein the axial array and the transaxial array are on adjacent sides.

16. A method according to claim 14, wherein the detector further includes a plurality of reflective partitions interspersed among the scintillator pixels.

17. A method according to claim 14, wherein the axial and transaxial arrays are linear.

18. A method according to claim 14, wherein the acquiring step includes reading out an event from the axial array, and reading out the event from the transaxial array.

19. A method according to claim 14, wherein the image is 3 dimensional (3-D).

* * * * *